United States Patent
Lins

(10) Patent No.: US 8,814,907 B2
(45) Date of Patent: Aug. 26, 2014

(54) SURGICAL IMPLANT DEVICE FOR THE TRANSLATION AND FUSION OF A FACET JOINT OF THE SPINE

(75) Inventor: Robert E. Lins, Boca Raton, FL (US)

(73) Assignee: LRAD, LLC, Boca Raton, FL (US)

( * ) Notice: Subject to any disclaimer, the term of this patent is extended or adjusted under 35 U.S.C. 154(b) by 147 days.

(21) Appl. No.: 12/875,374

(22) Filed: Sep. 3, 2010

(65) Prior Publication Data

US 2011/0054530 A1 Mar. 3, 2011

Related U.S. Application Data

(60) Provisional application No. 61/239,594, filed on Sep. 3, 2009.

(51) Int. Cl.
*A61B 17/00* (2006.01)

(52) U.S. Cl.
USPC .......................................... 606/247

(58) Field of Classification Search
USPC ............ 606/246–249, 304; 623/17.12–17.15, 623/17.11, 17.16
See application file for complete search history.

(56) References Cited

U.S. PATENT DOCUMENTS

| | | | | |
|---|---|---|---|---|
| 5,800,550 | A * | 9/1998 | Sertich ........................ | 623/17.16 |
| 6,371,987 | B1 * | 4/2002 | Weiland et al. ............. | 623/17.11 |
| 6,770,096 | B2 * | 8/2004 | Bolger et al. ............... | 623/17.16 |
| 7,699,878 | B2 * | 4/2010 | Pavlov et al. ................ | 606/279 |
| 7,708,761 | B2 | 5/2010 | Petersen | |
| 8,070,819 | B2 * | 12/2011 | Aferzon et al. ............ | 623/17.16 |
| 8,133,261 | B2 * | 3/2012 | Fisher et al. .................. | 606/247 |
| 8,162,981 | B2 * | 4/2012 | Vestgaarden ................. | 606/247 |
| 8,197,513 | B2 * | 6/2012 | Fisher et al. ................. | 606/247 |
| 2002/0128717 | A1 * | 9/2002 | Alfaro et al. ............... | 623/17.16 |
| 2003/0088251 | A1 * | 5/2003 | Braun et al. ..................... | 606/73 |
| 2004/0015172 | A1 * | 1/2004 | Biedermann et al. ........... | 606/73 |
| 2004/0138751 | A1 * | 7/2004 | Michelson ................. | 623/17.11 |
| 2005/0149193 | A1 * | 7/2005 | Zucherman et al. ....... | 623/17.11 |
| 2006/0058876 | A1 * | 3/2006 | McKinley .................. | 623/17.11 |
| 2006/0064099 | A1 * | 3/2006 | Pavlov et al. .................... | 606/72 |
| 2006/0111782 | A1 * | 5/2006 | Petersen .................... | 623/17.11 |
| 2006/0190081 | A1 * | 8/2006 | Kraus et al. ................ | 623/17.11 |
| 2008/0015582 | A1 | 1/2008 | DiPoto et al. | |
| 2008/0103512 | A1 * | 5/2008 | Gately .......................... | 606/151 |
| 2008/0132949 | A1 * | 6/2008 | Aferzon et al. .............. | 606/246 |
| 2008/0255666 | A1 * | 10/2008 | Fisher et al. ............... | 623/17.16 |
| 2009/0036927 | A1 | 2/2009 | Vestgaarden | |

(Continued)

FOREIGN PATENT DOCUMENTS

WO WO/2006/057943 6/2006

*Primary Examiner* — Jan Christopher Merene
(74) *Attorney, Agent, or Firm* — Clements Bernard PLLC; Christopher L. Bernard; Lawrence A. Baratta, Jr.

(57) ABSTRACT

The present invention provides a surgical implant device and method for the translation/distraction and subsequent stabilization/fusion of a facet joint of a spine, including: a body that is selectively disposed at least partially between articulating surfaces of the facet joint; and one or more protruding structures disposed about the body, wherein, when the body is selectively rotated, the one or more protruding surfaces are configured to engage the articulating surfaces of the facet joint and move them with respect to one another. Optionally, the surgical implant device also includes a joint-spanning structure coupled to the body, wherein the joint-spanning structure is configured to substantially fill a space between the articulating surfaces of the facet joint and hold it in a moved configuration.

4 Claims, 11 Drawing Sheets

(56) References Cited

U.S. PATENT DOCUMENTS

| | | |
|---|---|---|
| 2009/0076551 A1 | 3/2009 | Petersen |
| 2009/0099601 A1* | 4/2009 | Aferzon et al. .............. 606/246 |
| 2009/0164020 A1* | 6/2009 | Janowski et al. .......... 623/17.16 |
| 2009/0234397 A1 | 9/2009 | Petersen |
| 2009/0306671 A1* | 12/2009 | McCormack et al. .......... 606/90 |
| 2009/0312763 A1* | 12/2009 | McCormack et al. .......... 606/83 |
| 2010/0121378 A1* | 5/2010 | Malek ........................... 606/247 |
| 2010/0137910 A1 | 6/2010 | Cawley et al. |
| 2010/0191241 A1* | 7/2010 | McCormack et al. .......... 606/83 |
| 2011/0160772 A1 | 6/2011 | Arcenio et al. |
| 2011/0230912 A1* | 9/2011 | Dennis ......................... 606/247 |

\* cited by examiner

SURGICAL IMPLANT DEVICE FOR THE TRANSLATION AND FUSION OF A FACET JOINT OF THE SPINE

CROSS-REFERENCE TO RELATED APPLICATION

The present patent application/patent claims the benefit of priority of co-pending U.S. Provisional Patent Application No. 61/239,594, filed on Sep. 3, 2009, and entitled "SURGICAL IMPLANT DEVICE FOR THE TRANSLATION AND FUSION OF A FACET JOINT OF THE SPINE," the contents of which are incorporated in full by reference herein.

FIELD OF THE INVENTION

The present invention relates generally to a novel surgical implant device for treating spinal stenosis, facet arthropathy, degenerative disc disease, and the like. More specifically, the present invention relates to a novel surgical implant device for the translation/distraction and subsequent stabilization/fusion of a facet joint of the spine in the treatment of such conditions.

BACKGROUND OF THE INVENTION

There are a variety of conventional surgical implant devices and methodologies for stabilizing/fusing a facet joint of the spine. Most of these devices and methodologies involve drilling between and across the articulating surfaces of the facet joint while un-translated/non-distracted and inserting a plug or other stabilization structure in the drilled hole(s). Some of these device and methodologies involve placing a bolt or other retention structure through (i.e. substantially perpendicularly across) or about the articulating surfaces of the facet joint while un-translated/non-distracted. These conventional surgical implant devices and methodologies, however, suffer from a number of significant shortcomings and often fail to adequately address patient symptoms.

BRIEF SUMMARY OF THE INVENTION

It is desirable, in many applications, to translate/distract the facet joint before stabilizing/fusing it, especially in the lumbar spine. This may be accomplished, for example, by placing a surgical implant device in the facet joint and rotating it, thus displacing the articulating surfaces of the facet joint with respect to one another with a translation motion and/or a distraction motion. Such a procedure may be carried out both left and right at each level of the spine.

Advantageously, such displacement increases the size of the foramen, where the nerve roots exit the central spinal canal, thus addressing foraminal stenosis, which may cause leg symptoms. Such displacement also addresses central spinal canal stenosis by unbuckling or stretching out the redundant ligamentum flavum which connect each spinal segment posteriorly. Such displacement further unloads the posterior aspect of the intervertebral disc posteriorly, and may be used to address underlying degenerative disc disease, in addition to lumbar spinal stenosis, facet arthropathy (i.e. facet arthritis), and the like.

The surgical procedures of the present invention may be performed percutaneously or through two small incisions on the back, one on each side. An elongated device with a sharp point and a plurality of concentrically-arranged friction structures, for example, is inserted into the facet joint and rotated, thus providing translation/distraction. A retention sleeve is then slid down the elongated device and into or adjacent to and engaging the facet joint to maintain the facet joint in translation/distraction while the elongated device is removed. Subsequently or alternatively, a hole is drilled between and across the articulating surfaces of the facet joint through the retention sleeve and a plug or other novel surgical implant device is tamped into the hole to maintain the facet joint in translation/distraction. This later function may be accomplished using the retention sleeve itself, in the case that it is simply a toothed retention washer or the like. Alternatively, the novel surgical implant device may be inserted into the facet joint, rotated to translate/distract the facet joint, and then remain in place itself (optionally after additional seating) to hold the facet joint in the desired configuration. This surgical implant device may be a detachable end portion of the elongated device, for example.

Alternatively, after translating/distracting, a stellate/snowflake-shaped tamp may be impacted into and across the facet joint to create an outline for a serrated surgical implant device to subsequently be impacted into this outline. This provides an interference fit and prevents unwinding of the facet joint. Various surgical implant device configurations are contemplated, illustrated, and described herein, including various friction structures and various other structures that aide in the translation/distraction of the facet joint and variously fill the "gap" therein.

The goal of the present invention is to stabilize/fuse the facet joint in a desirable configuration that alleviates a given physical ailment or condition. The various surgical implant devices of the present invention may be made of machined allograft (i.e. bony) material, a surgically-implantable polymeric material, a surgically-implantable ceramic material, a surgically-implantable metallic material, etc., and may include one or more holes or pores for the impaction of another material that promotes the fusion of the superior and inferior facets of a facet joint.

In one exemplary embodiment, the present invention provides a surgical implant device for the translation/distraction and subsequent stabilization/fusion of a facet joint of a spine, including: a body that is selectively disposed at least partially between articulating surfaces of the facet joint; and one or more protruding structures disposed about the body, wherein, when the body is selectively rotated, the one or more protruding surfaces are configured to engage the articulating surfaces of the facet joint and move them with respect to one another. Optionally, the surgical implant device also includes a joint-spanning structure coupled to the body, wherein the joint-spanning structure is configured to substantially fill a space between the articulating surfaces of the facet joint and hold it in a moved configuration.

In another exemplary embodiment, the present invention provides a surgical implant method for the translation/distraction and subsequent stabilization/fusion of a facet joint of a spine, including: selectively disposing a body at least partially between articulating surfaces of the facet joint; and selectively rotating the body such that one or more protruding structures disposed about the body engage the articulating surfaces of the facet joint and move them with respect to one another. Optionally, the method also includes providing a joint-spanning structure coupled to the body, wherein the joint-spanning structure is configured to substantially fill a space between the articulating surfaces of the facet joint and hold it in a moved configuration.

In a further exemplary embodiment, the present invention provides a surgical implant system for the translation/distraction and subsequent stabilization/fusion of a facet joint of a spine, including: a tool that is selectively disposed at least partially between articulating surfaces of the facet joint; and one or more protruding structures disposed about the tool, wherein, when the tool is selectively rotated, the one or more protruding surfaces are configured to engage the articulating surfaces of the facet joint and move them with respect to one another. The surgical implant system also includes a sheath disposed about the tool, wherein the sheath is selectively slid down the tool to engage the facet joint to maintain the facet joint in a moved configuration while the tool is removed. The surgical implant system further includes a surgical implant device that is selectively disposed at least partially between articulating surfaces of the facet joint to maintain the facet joint in the moved configuration while the sheath is removed.

In a still further exemplary embodiment, the present invention provides a surgical implant method for the translation/distraction and subsequent stabilization/fusion of a facet joint of a spine, including: moving a first articulating surface of the facet joint with respect to a second articulating surface of the facet joint; forming a cut-away portion of each of the articulating surfaces of the facet joint; and disposing a surgical implant device in the cut-away portion of each of the articulating surfaces of the facet joint to prevent unwinding thereof.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
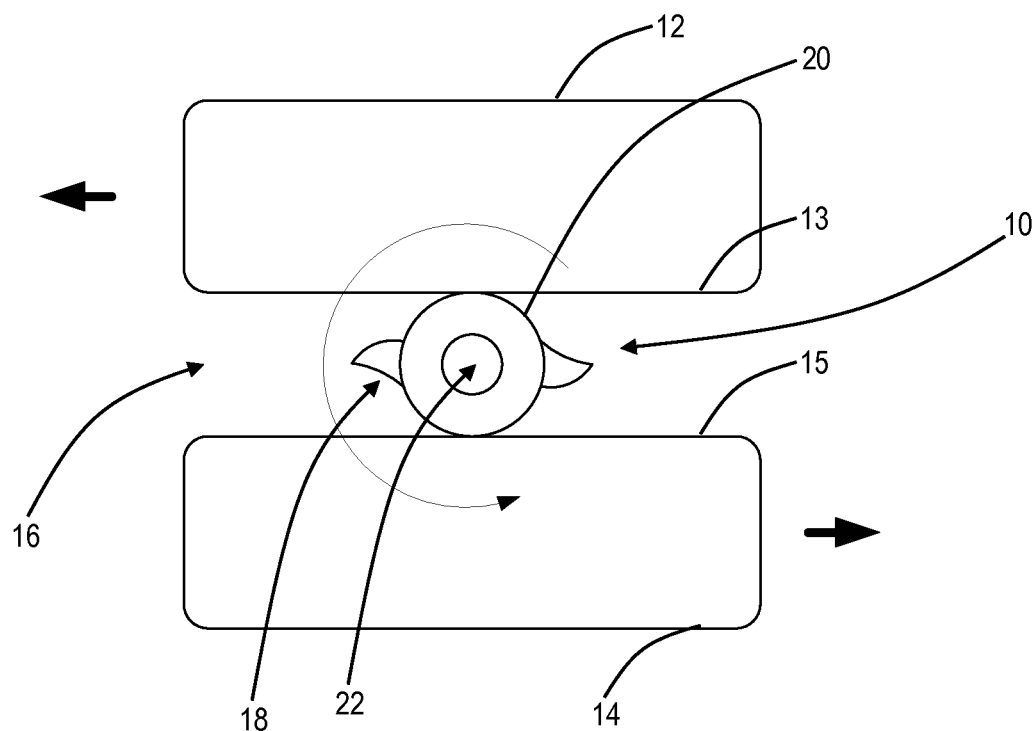
FIG. 1 is a schematic diagram illustrating one exemplary embodiment of the facet implant device of the present invention, and one exemplary embodiment of the facet translation/fusion method of the present invention.

Referring to FIG. 1, in one exemplary embodiment of the present invention, the facet implant device 10 is disposed between the superior facet 12 and the inferior facet 14 of the facet joint 16 of a spine. The facet implant device 10 includes one or more protruding structures 18 or friction surfaces that engage the articulating surfaces 13, 15 of the facet joint 16 when the facet implant device 10 is rotated in the facet joint 16, the protruding structures 18 first contacting the articulating surfaces 13, 15, then grabbing them, then translating/distracting them with respect to one another, and then holding them securely in this translated/distracted configuration. In the embodiment illustrated, the facet implant device 10 includes a substantially-cylindrical body 20 and two or four substantially-triangular or fin-like protruding structures 18 that have sharp surfaces or edges for engaging the articulating surfaces 13, 15, although other suitable assemblies are contemplated herein. The facet implant device 10 has over all dimensions on the order of several millimeters, and may be made of machined allograft (i.e. bony) material, a surgically-implantable polymeric material, a surgically-implantable ceramic material, a surgically-implantable metallic material, etc. The facet implant device 10 may include one or more holes or pores 22 along its major axis and/or perpendicular to its major axis through the body 20 thereof for the impaction of another material that promotes the fusion of the superior and inferior facets 12, 14 of the facet joint 16. In addition, the body 20 of the facet implant device 10 may have a threaded portion or other attachment means for receiving one or more tools by which it is tamped into the facet joint 16 and/or rotated.

Figure 2:
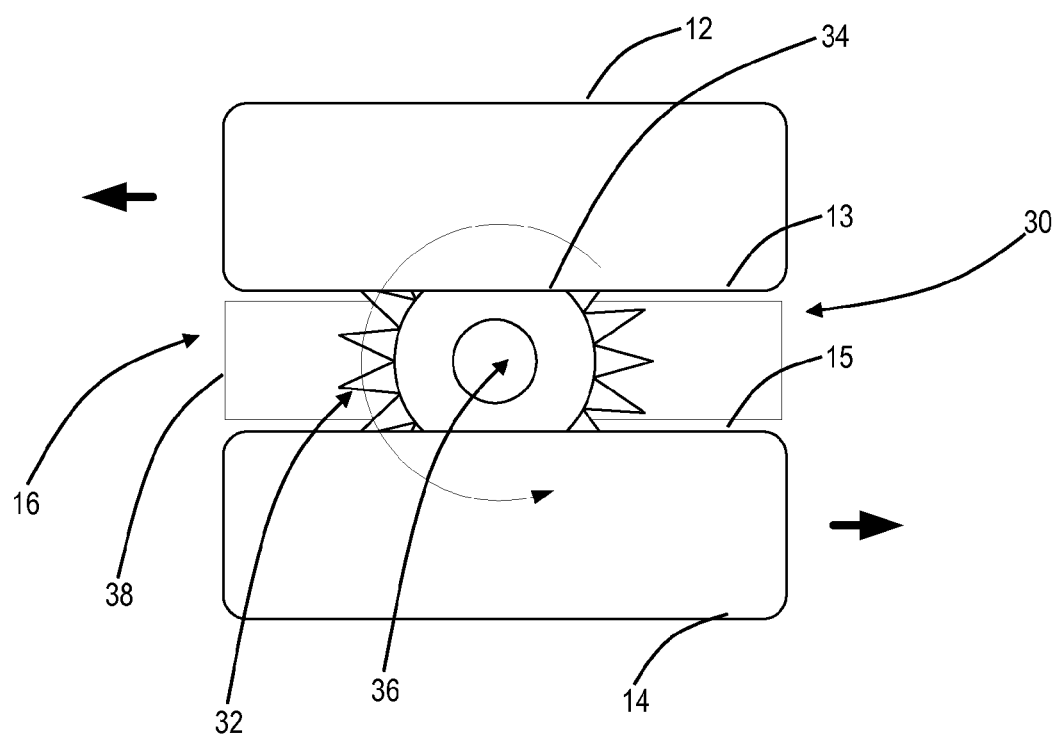
FIG. 2 is a schematic diagram illustrating another exemplary embodiment of the facet implant device of the present invention, and another exemplary embodiment of the facet translation/fusion method of the present invention.

Referring to FIG. 2, in another exemplary embodiment of the present invention, the facet implant device 30 is disposed between the superior facet 12 and the inferior facet 14 of the facet joint 16 of a spine. The facet implant device 30 includes one or more protruding structures 32 or friction surfaces that engage the articulating surfaces 13, 15 of the facet joint 16 when the facet implant device 30, or a portion thereof, is rotated in the facet joint 16, the protruding structures 32 first contacting the articulating surfaces 13, 15, then grabbing them, then translating/distracting them with respect to one another, and then holding them securely in this translated/distracted configuration. In the embodiment illustrated, the facet implant device 30 includes a substantially-cylindrical body 34 and a plurality of substantially-triangular or tooth-like protruding structures 32 that have sharp surfaces or edges for engaging the articulating surfaces 13, 15, although other suitable assemblies are contemplated herein. The facet implant device 30 has over all dimensions on the order of several millimeters, and may be made of machined allograft (i.e. bony) material, a surgically-implantable polymeric material, a surgically-implantable ceramic material, a surgically-implantable metallic material, etc. The facet implant device 30 may include one or more holes or pores 36 along its major axis and/or perpendicular to its major axis through the body 34 thereof for the impaction of another material that promotes the fusion of the superior and inferior facets 12, 14 of the facet joint 16. In addition, the body 34 of the facet implant device 30 may have a threaded portion or other attachment means for receiving one or more tools by which it is tamped into the facet joint 16 and/or rotated. In the embodiment illustrated, the facet implant device 30 also includes a joint-spanning structure 38 coupled to the body 34. This joint-spanning structure 38 may or may not rotate with the body 34 when it is rotated in the facet joint 16 and, in any case, is used to substantially fill the facet joint 16, providing friction surfaces that prevent the articulating surfaces 13, 15 from sliding with respect to one another once translation/distraction has been achieved. Accordingly, the joint-spanning structure 38 may have a substantially-rectangular or other suitable shape and a thickness on the order of several millimeters.

Figure 3:
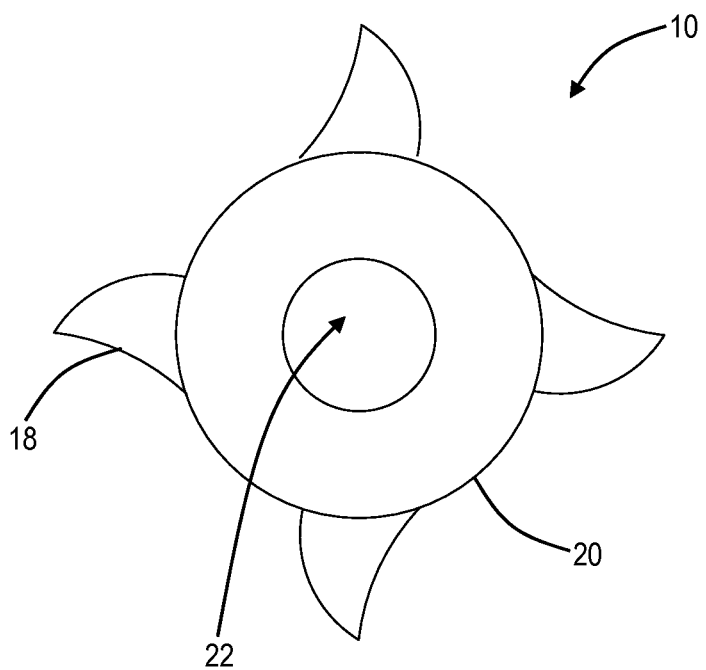
FIG. 3 is a schematic diagram illustrating one exemplary embodiment of the facet implant device of the present invention.

Referring to FIG. 3, in one exemplary embodiment of the present invention, the facet implant device 10 includes one or more protruding structures 18 or friction surfaces that engage the articulating surfaces 13, 15 (FIGS. 1 and 2) of the facet joint 16 (FIGS. 1 and 2) when the facet implant device 10 is rotated in the facet joint 16, the protruding structures 18 first contacting the articulating surfaces 13, 15, then grabbing them, then translating/distracting them with respect to one another, and then holding them securely in this translated/distracted configuration. In the embodiment illustrated, the facet implant device 10 includes a substantially-cylindrical body 20 and two or four substantially-triangular or fin-like protruding structures 18 that have sharp surfaces or edges for engaging the articulating surfaces 13, 15, although other suitable assemblies are contemplated herein. The facet implant device 10 has over all dimensions on the order of several millimeters, and may be made of machined allograft (i.e. bony) material, a surgically-implantable polymeric material, a surgically-implantable ceramic material, a surgically-implantable metallic material, etc. The facet implant device 10 may include one or more holes or pores 22 along its major axis and/or perpendicular to its major axis through the body 20 thereof for the impaction of another material that promotes the fusion of the superior and inferior facets 12, 14 (FIGS. 1 and 2) of the facet joint 16. In addition, the body 20 of the facet implant device 10 may have a threaded portion or other attachment means for receiving one or more tools by which it is tamped into the facet joint 16 and/or rotated.

Figure 4:
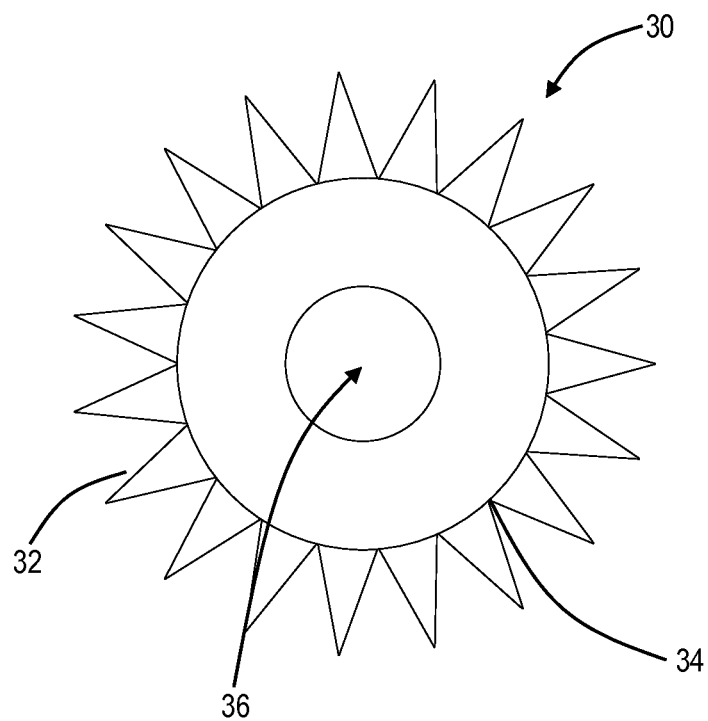
FIG. 4 is a schematic diagram illustrating another exemplary embodiment of the facet implant device of the present invention.

Referring to FIG. 4, in another exemplary embodiment of the present invention, the facet implant device 30 includes one or more protruding structures 32 or friction surfaces that engage the articulating surfaces 13, 15 (FIGS. 1 and 2) of the facet joint 16 (FIGS. 1 and 2) when the facet implant device 30 is rotated in the facet joint 16, the protruding structures 32 first contacting the articulating surfaces 13, 15, then grabbing them, then translating/distracting them with respect to one another, and then holding them securely in this translated/distracted configuration. In the embodiment illustrated, the facet implant device 30 includes a substantially-cylindrical body 34 and a plurality of substantially-triangular or tooth-like protruding structures 32 that have sharp surfaces or edges for engaging the articulating surfaces 13, 15, although other suitable assemblies are contemplated herein. The facet implant device 30 has over all dimensions on the order of several millimeters, and may be made of machined allograft (i.e. bony) material, a surgically-implantable polymeric material, a surgically-implantable ceramic material, a surgically-implantable metallic material, etc. The facet implant device 30 may include one or more holes or pores 36 along its major axis and/or perpendicular to its major axis through the body 34 thereof for the impaction of another material that promotes the fusion of the superior and inferior facets 12, 14 (FIGS. 1 and 2) of the facet joint 16. In addition, the body 34 of the facet implant device 30 may have a threaded portion or other attachment means for receiving one or more tools by which it is tamped into the facet joint 16 and/or rotated.

Figure 5:
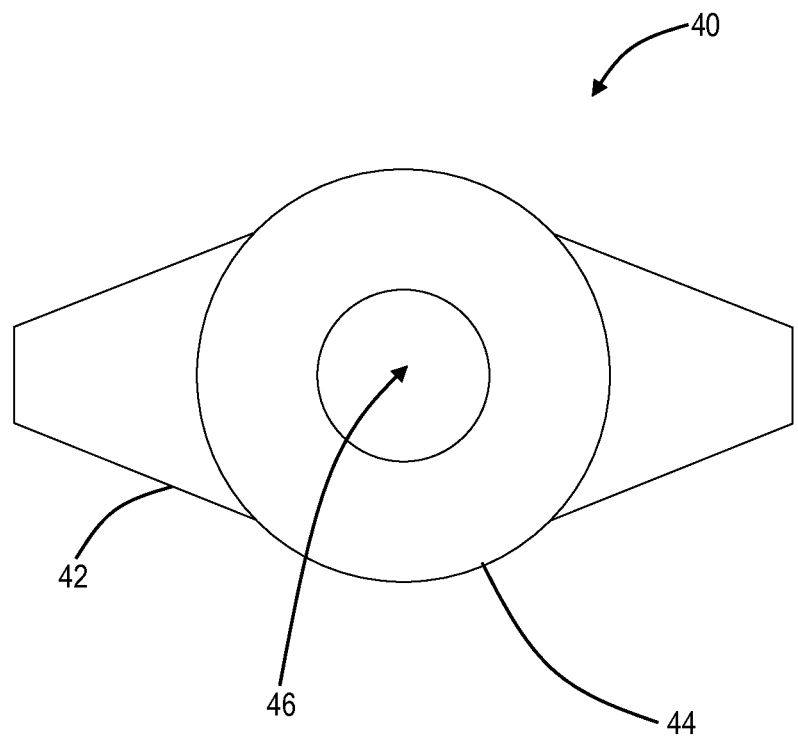
FIG. 5 is a schematic diagram illustrating a further exemplary embodiment of the facet implant device of the present invention.

Referring to FIG. 5, in a further exemplary embodiment of the present invention, the facet implant device 40 includes one or more protruding structures 42 or friction surfaces that engage the articulating surfaces 13, 15 (FIGS. 1 and 2) of the facet joint 16 (FIGS. 1 and 2) when the facet implant device 40 is rotated in the facet joint 16, the protruding structures 42 first contacting the articulating surfaces 13, 15, then grabbing them, then translating/distracting them with respect to one another, and then holding them securely in this translated/distracted configuration. In the embodiment illustrated, the facet implant device 40 includes a substantially-cylindrical body 44 and two substantially-trapezoidal or fin-like protruding structures 42 that have sharp surfaces or edges for engaging the articulating surfaces 13, 15, although other suitable assemblies are contemplated herein. The facet implant device 40 has over all dimensions on the order of several millimeters, and may be made of machined allograft (i.e. bony) material, a surgically-implantable polymeric material, a surgically-implantable ceramic material, a surgically-implantable metallic material, etc. The facet implant device 40 may include one or more holes or pores 46 along its major axis and/or perpendicular to its major axis through the body 44 thereof for the impaction of another material that promotes the fusion of the superior and inferior facets 12, 14 (FIGS. 1 and 2) of the facet joint 16. In addition, the body 44 of the facet implant device 40 may have a threaded portion or other attachment means for receiving one or more tools by which it is tamped into the facet joint 16 and/or rotated.

Figure 6:
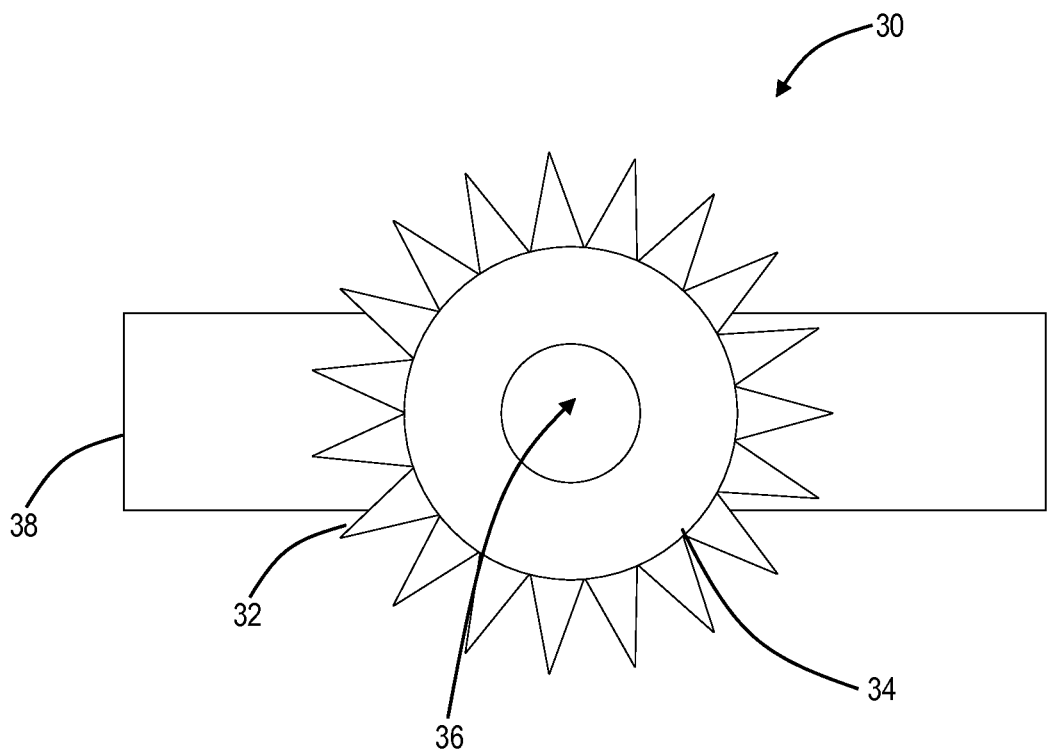
FIG. 6 is a schematic diagram illustrating a still further exemplary embodiment of the facet implant device of the present invention.

Referring to FIG. 6, in a still further exemplary embodiment of the present invention, the facet implant device 30 includes one or more protruding structures 32 or friction surfaces that engage the articulating surfaces 13, 15 (FIGS. 1 and 2) of the facet joint 16 (FIGS. 1 and 2) when the facet implant device 30, or a portion thereof, is rotated in the facet joint 16, the protruding structures 32 first contacting the articulating surfaces 13, 15, then grabbing them, then translating/distracting them with respect to one another, and then holding them securely in this translated/distracted configuration. In the embodiment illustrated, the facet implant device 30 includes a substantially-cylindrical body 34 and a plurality of substantially-triangular or tooth-like protruding structures 32 that have sharp surfaces or edges for engaging the articulating surfaces 13, 15, although other suitable assemblies are contemplated herein. The facet implant device 30 has over all dimensions on the order of several millimeters, and may be made of machined allograft (i.e. bony) material, a surgically-implantable polymeric material, a surgically-implantable ceramic material, a surgically-implantable metallic material, etc. The facet implant device 30 may include one or more holes or pores 36 along its major axis and/or perpendicular to its major axis through the body 34 thereof for the impaction of another material that promotes the fusion of the superior and inferior facets 12, 14 (FIGS. 1 and 2) of the facet joint 16. In addition, the body 34 of the facet implant device 30 may have a threaded portion or other attachment means for receiving one or more tools by which it is tamped into the facet joint 16 and/or rotated. In the embodiment illustrated, the facet implant device 30 also includes a joint-spanning structure 38 coupled to the body 34. This joint-spanning structure 38 may or may not rotate with the body 34 when it is rotated in the facet joint 16 and, in any case, is used to substantially fill the facet joint 16, providing friction surfaces that prevent the articulating surfaces 13, 15 from sliding with respect to one another once translation/distraction has been achieved. Accordingly, the joint-spanning structure 38 may have a substantially-rectangular or other suitable shape and a thickness on the order of several millimeters. In an alternative embodiment, neither the body 34 or the joint-spanning structure 38 may be rotated, but may simply be used to fill the facet joint 16 and any manufactured recesses and keep the facet joint 16 from unwinding. In this embodiment, only the upper and lower portions of the body 34 need have teeth or fins 32, for example.

Figure 7:
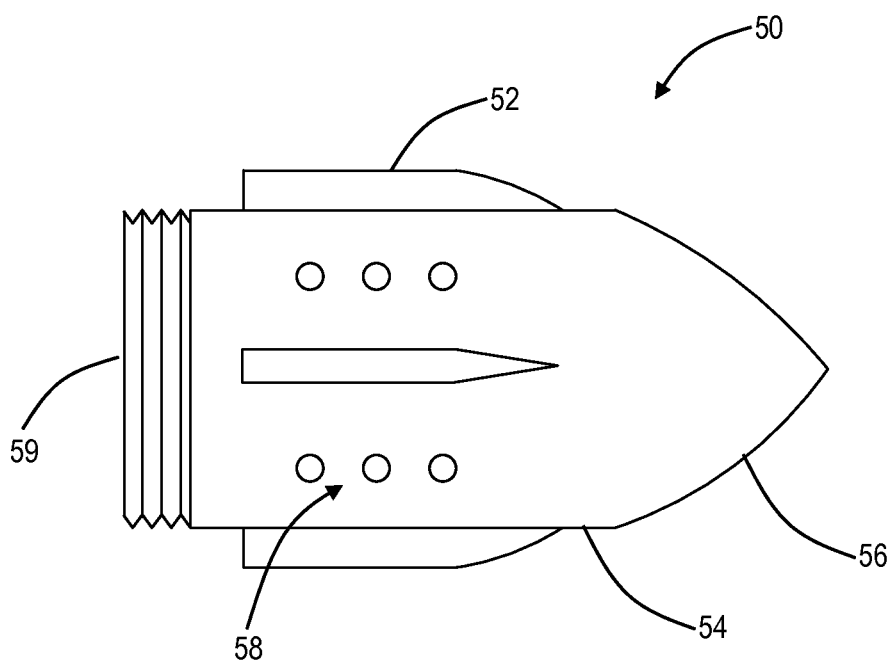
FIG. 7 is a schematic diagram illustrating a still further exemplary embodiment of the facet implant device of the present invention.

Referring to FIG. 7, in a still further exemplary embodiment of the present invention, the facet implant device 50 includes one or more protruding structures 52 or friction surfaces that engage the articulating surfaces 13, 15 (FIGS. 1 and 2) of the facet joint 16 (FIGS. 1 and 2) when the facet implant device 50 is rotated in the facet joint 16, the protruding structures 52 first contacting the articulating surfaces 13, 15, then grabbing them, then translating/distracting them with respect to one another, and then holding them securely in this translated/distracted configuration. In the embodiment illustrated, the facet implant device 50 includes a substantially-cylindrical body 54, a substantially-conical insertion tip 56, and two or four substantially-triangular or fin-like protruding structures 52 that have sharp surfaces or edges for engaging the articulating surfaces 13, 15, although other suitable assemblies are contemplated herein. The facet implant device 50 has over all dimensions on the order of several millimeters, and may be made of machined allograft (i.e. bony) material, a surgically-implantable polymeric material, a surgically-implantable ceramic material, a surgically-implantable metallic material, etc. The facet implant device 50 may include one or more holes or pores 58 along its major axis and/or perpendicular to its major axis through the body 54 thereof for the impaction of another material that promotes the fusion of the superior and inferior facets 12, 14 (FIGS. 1 and 2) of the facet joint 16. In addition, the body 54 of the facet implant device 50 may have a threaded portion 59 or other attachment means for receiving one or more tools by which it is tamped into the facet joint 16 and/or rotated. Optionally, one of the tools may act as a plunger through which fusion-promoting material is introduced into the facet implant device 50.

Figure 8:
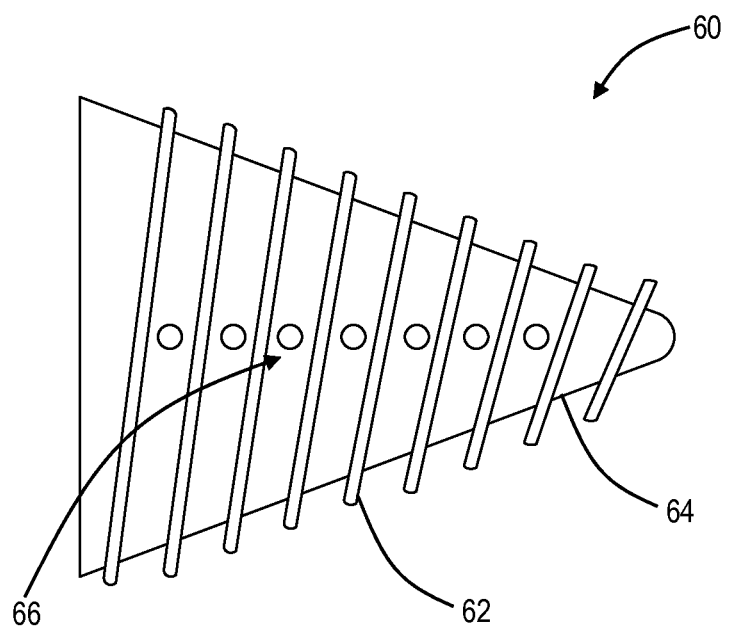
FIG. 8 is a schematic diagram illustrating a still further exemplary embodiment of the facet implant device of the present invention.

Referring to FIG. 8, in a still further exemplary embodiment of the present invention, the facet implant device 60 includes one or more protruding structures 62 or friction surfaces disposed concentrically there about (such as threads or the like) that engage the articulating surfaces 13, 15 (FIGS. 1 and 2) of the facet joint 16 (FIGS. 1 and 2) when the facet implant device 60 is rotated in the facet joint 16, the protruding structures 62 first contacting the articulating surfaces 13, 15, then grabbing them, then translating/distracting them with respect to one another, and then holding them securely in this translated/distracted configuration. In the embodiment illustrated, the facet implant device 60 includes a substantially-conical body 64 and a plurality of protruding structures 62 that have sharp surfaces or edges for engaging the articulating surfaces 13, 15, although other suitable assemblies are contemplated herein. The facet implant device 60 has over all dimensions on the order of several millimeters, and may be made of machined allograft (i.e. bony) material, a surgically-implantable polymeric material, a surgically-implantable ceramic material, a surgically-implantable metallic material, etc. The facet implant device 60 may include one or more holes or pores 66 along its major axis and/or perpendicular to its major axis through the body 64 thereof for the impaction of another material that promotes the fusion of the superior and inferior facets 12, 14 (FIGS. 1 and 2) of the facet joint 16. In addition, the body 64 of the facet implant device 60 may have a threaded portion or other attachment means for receiving one or more tools by which it is tamped into the facet joint 16 and/or rotated.

Figure 9:
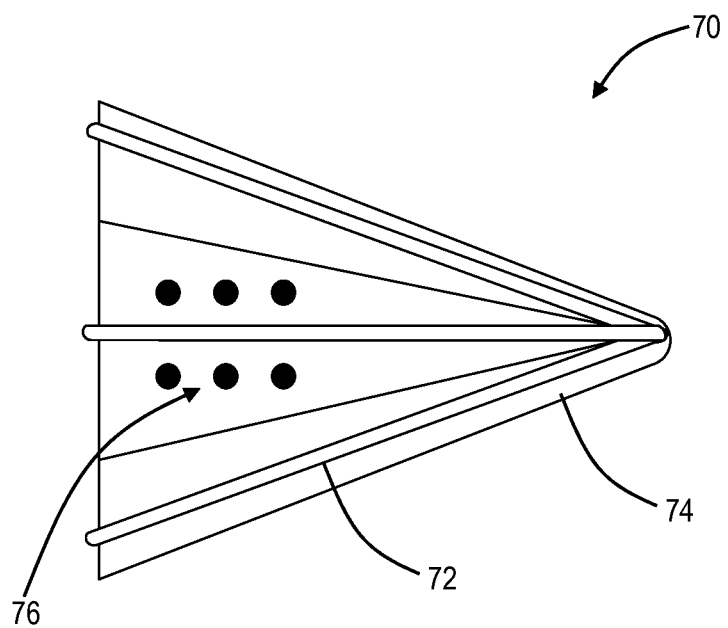
FIG. 9 is a schematic diagram illustrating a still further exemplary embodiment of the facet implant device of the present invention.

Referring to FIG. 9, in a still further exemplary embodiment of the present invention, the facet implant device 70 includes one or more protruding structures 72 or friction surfaces disposed axially there about (such as ridges or the like) that engage the articulating surfaces 13, 15 (FIGS. 1 and 2) of the facet joint 16 (FIGS. 1 and 2) when the facet implant device 70 is rotated in the facet joint 16, the protruding structures 72 first contacting the articulating surfaces 13, 15, then grabbing them, then translating/distracting them with respect to one another, and then holding them securely in this translated/distracted configuration. In the embodiment illustrated, the facet implant device 70 includes a substantially-conical body 74 and a plurality of protruding structures 72 that have sharp surfaces or edges for engaging the articulating surfaces 13, 15, although other suitable assemblies are contemplated herein. The facet implant device 70 has over all dimensions on the order of several millimeters, and may be made of machined allograft (i.e. bony) material, a surgically-implantable polymeric material, a surgically-implantable ceramic material, a surgically-implantable metallic material, etc. The facet implant device 70 may include one or more holes or pores 76 along its major axis and/or perpendicular to its major axis through the body 74 thereof for the impaction of another material that promotes the fusion of the superior and inferior facets 12, 14 (FIGS. 1 and 2) of the facet joint 16. In addition, the body 74 of the facet implant device 70 may have a threaded portion or other attachment means for receiving one or more tools by which it is tamped into the facet joint 16 and/or rotated.

It should be noted that, in all of the above embodiments, the articulating surfaces 13, 15 (FIGS. 1 and 2) of the facet joint 16 (FIGS. 1 and 2) may be cut, chiseled, gouged, or otherwise formed to substantially conform to the various surfaces of the various facet implant devices. The facet implant devices may also be advanced into the facet joint 16 upon rotation, or may be inserted, rotated to perform translation/distraction, and then further inserted to lock the facet joint 16. Any combination of elements/steps is possible.

Figure 10:
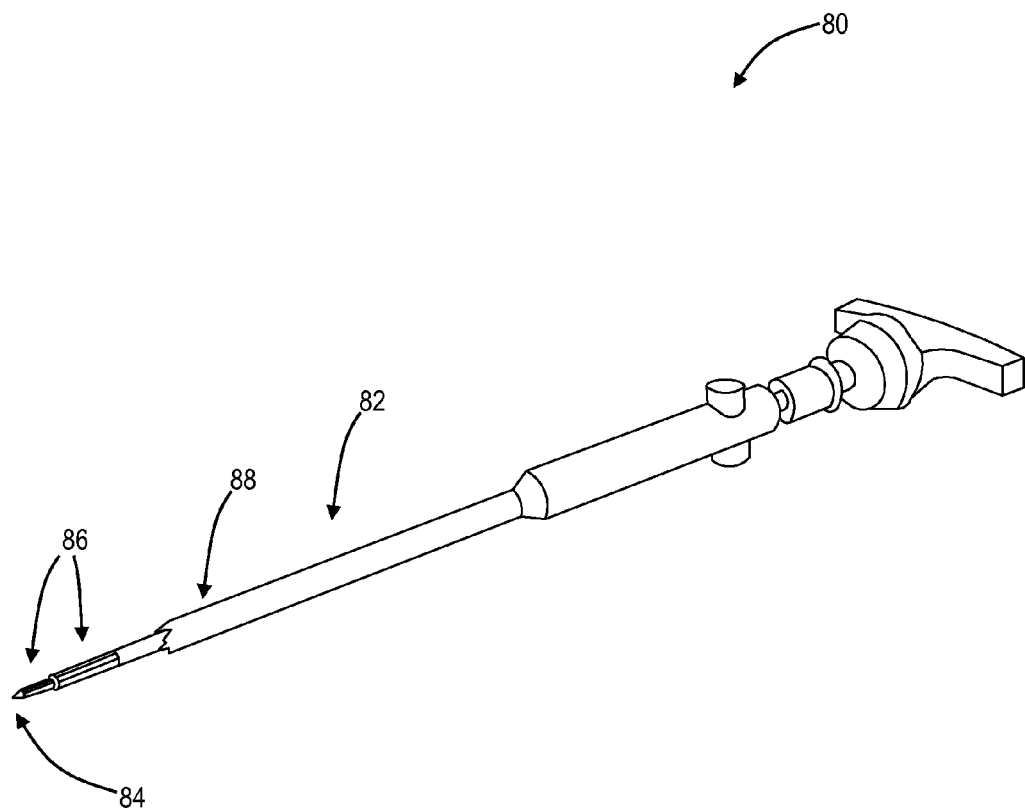
FIG. 10 is a perspective diagram illustrating one exemplary embodiment of the facet implant device tool assembly of the present invention.
Figure 11:
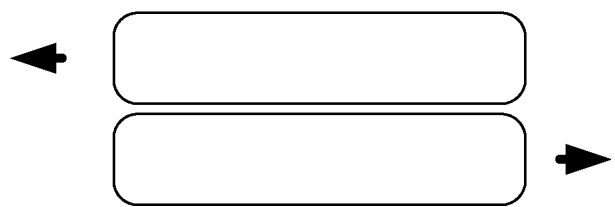
FIG. 11 is a series of schematic diagrams illustrating another exemplary embodiment of the facet translation/fusion method of the present invention.
Figure 11:
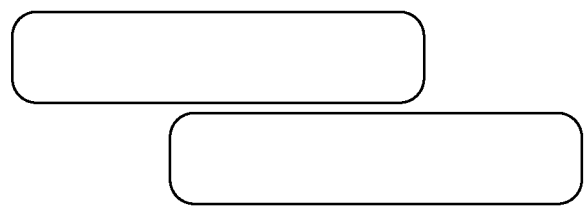
Figure 11:
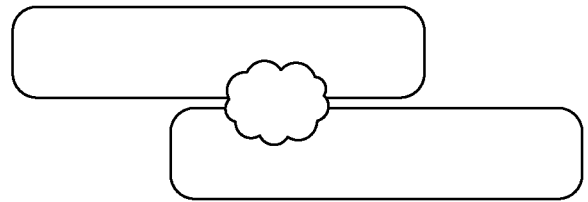
Figure 11:
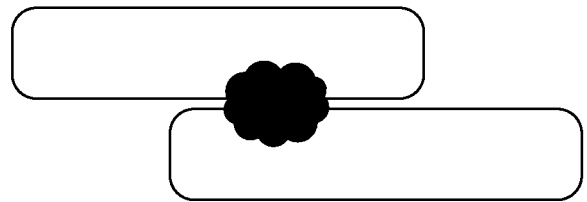

FIG. 10 is a perspective diagram illustrating one exemplary embodiment of the facet implant device tool assembly 80 of the present invention. An elongated device 82 with a sharp point 84 and a plurality of concentrically-arranged friction structures 86, for example, is inserted into the facet joint 16 (FIGS. 1 and 2) and rotated, thus providing translation/distraction. A retention sleeve 88 is then slid down the elongated device and into or adjacent to and engaging the facet joint 16 to maintain the facet joint 16 in translation/distraction while the elongated device 82 is removed. Subsequently or alternatively, a hole is drilled between and across the articulating surfaces 13, 15 (FIGS. 1 and 2) of the facet joint 16 through the retention sleeve 88 and a plug or other novel surgical implant device is tamped into the hole to maintain the facet joint 16 in translation/distraction. This later function may be accomplished using the retention sleeve 88 itself, in the case that it is simply a toothed retention washer or the like. Alternatively, the novel surgical implant device may be inserted into the facet joint 16, rotated to translate/distract the facet joint, and then remain in place itself (optionally after additional seating) to hold the facet joint 16 in the desired configuration. This surgical implant device may be a detachable end portion of the elongated device 82, for example. Alternatively, after translating/distracting, a stellate/snowflake-shaped (or other patterned) tamp may be impacted into and across the facet joint 16 to create an outline for a serrated surgical implant device to subsequently be impacted into this outline. This provides an interference fit and prevents unwinding of the facet joint 16. This facet translation/fusion method is illustrated in FIG. 11.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A surgical implant device for the translation/distraction and subsequent stabilization/fusion of a facet joint of a spine, comprising:
   a body comprising a major axis along the length thereof that is selectively disposed at least partially between and in direct physical contact with articulating surfaces of the facet joint; and
   a plurality of protruding structures disposed about the body, wherein, when the body is selectively rotated, the plurality of protruding structures rotate concentrically about the major axis of the body and are configured to engage the articulating surfaces of the facet joint and translate the articulating surfaces with respect to one another in a direction parallel to and along the articulating surfaces;
   wherein a first protruding structure on one side of the body moves in a first direction upon rotation of the body about the major axis thereof and translates a first articulating surface in the first direction and a second protruding structure on an opposite side of the body moves in a second direction substantially opposite the first direction upon rotation of the body about the major axis thereof and translates a second articulating surface in the second direction;
   wherein the plurality of protruding structures comprise elongate structures with tapering end portions and sharpened side portions, the elongate structures extending parallel to the major axis of the body for physically impacting into the articulating surfaces upon disposal of the body into the facet joint; and
   a joint-spanning structure coupled to the body, wherein the joint-spanning structure is configured to substantially fill a space between the articulating surfaces of the facet joint and hold it in a moved configuration.

2. The surgical implant device of claim 1, wherein the body comprises one of a substantially-cylindrical body and a substantially-conical body.

3. The surgical implant device of claim 1, wherein the body comprises one or more holes configured to hold a fusion-promoting material.

4. The surgical implant device of claim 1, wherein the plurality of protruding structures comprise a plurality of raised ridges, teeth, or fins.

* * * * *